(12) United States Patent
Germanaud et al.

(10) Patent No.: US 9,422,468 B2
(45) Date of Patent: Aug. 23, 2016

(54) COMPOSITION OF SPECIAL FLUID AND USE

(75) Inventors: Laurent Germanaud, Heyrieux (FR); Samia Lamrani-Kern, Le Perreux sur Marne (FR)

(73) Assignee: Total Marketing Services, Puteaux (FR)

( * ) Notice: Subject to any disclaimer, the term of this patent is extended or adjusted under 35 U.S.C. 154(b) by 325 days.

(21) Appl. No.: 13/441,177

(22) Filed: Apr. 6, 2012

(65) Prior Publication Data

US 2012/0264656 A1  Oct. 18, 2012

(30) Foreign Application Priority Data

Apr. 6, 2011 (FR) ...................................... 11 53005

(51) Int. Cl.
| | | |
|---|---|---|
| C10M 101/02 | (2006.01) |
| C09D 7/12 | (2006.01) |
| C11D 3/18 | (2006.01) |
| C09K 8/035 | (2006.01) |
| C09K 8/34 | (2006.01) |
| C10L 1/04 | (2006.01) |
| C10M 111/02 | (2006.01) |
| C10M 111/04 | (2006.01) |
| C11D 7/24 | (2006.01) |
| A61K 47/06 | (2006.01) |
| C09D 11/033 | (2014.01) |
| A61K 8/31 | (2006.01) |
| A61Q 19/00 | (2006.01) |
| C08L 93/00 | (2006.01) |

(52) U.S. Cl.
CPC ... C09K 8/34 (2013.01); A61K 8/31 (2013.01); A61K 47/06 (2013.01); A61Q 19/00 (2013.01); C08L 93/00 (2013.01); C09D 11/033 (2013.01); C10L 1/04 (2013.01); C10M 111/02 (2013.01); C10M 111/04 (2013.01); C11D 3/188 (2013.01); C11D 7/248 (2013.01); *A61K 2800/10* (2013.01); *C10M 2203/0206* (2013.01); *C10M 2203/045* (2013.01); *C10M 2203/1025* (2013.01); *C10M 2205/173* (2013.01)

(58) Field of Classification Search
CPC ........................................................ C09K 8/08
See application file for complete search history.

(56) References Cited

U.S. PATENT DOCUMENTS

| | | | | |
|---|---|---|---|---|
| 5,559,085 A * | 9/1996 | Duncan, Jr. ................... | 507/103 |
| 5,616,549 A | 4/1997 | Clark | |
| 6,093,861 A * | 7/2000 | Muntz .................. | C10M 127/02 585/13 |
| 7,592,295 B1 * | 9/2009 | Fisher et al. .................. | 507/110 |
| 7,691,792 B1 * | 4/2010 | Fisher et al. ................... | 508/110 |
| 2004/0023823 A1 | 2/2004 | Itoh et al. | |
| 2004/0102351 A1 | 5/2004 | Jansen | |
| 2008/0102211 A1 | 5/2008 | Matsuo et al. | |
| 2008/0171794 A1 * | 7/2008 | Yamamoto et al. ............ | 514/715 |
| 2010/0022417 A1 * | 1/2010 | Acunto ........................... | 507/90 |
| 2011/0287988 A1 * | 11/2011 | Fisher et al. ................... | 508/110 |
| 2012/0138508 A1 | 6/2012 | Okabe et al. | |

FOREIGN PATENT DOCUMENTS

| | | |
|---|---|---|
| EP | 1077675 | 2/2001 |
| EP | 1614411 A1 | 1/2006 |
| EP | 1946743 | 7/2008 |
| EP | 2062584 | 5/2009 |
| GB | 2287265 | 9/1995 |
| JP | S6484431 A | 3/1989 |
| JP | H05221880 A | 8/1993 |
| JP | H1036893 A | 2/1998 |
| JP | 2005023196 A | 1/2005 |
| WO | WO 2008/024488 | 2/2008 |
| WO | WO-2008024488 A2 | 2/2008 |
| WO | WO-2008/045555 | 4/2008 |

OTHER PUBLICATIONS

Sasol North America Inc, LPA SOLVENTS, Jun. 15, 2009, p. 1.*
Penreco, May 10, 2007, LVT-200 MSDS Sheet, 1-5.*
French Search Report and Written Opinion in Priority Application (FR 11 53 005).
Colombian Office Action issued Jul. 30, 2014.
Cheng, G., "De-aromatized solvent oil and development of hydrogen production technology of the de-aromatized solvent oil," Petroleum Products Application Research, No. 1, Feb. 2011, pp. 55-59.
Ma, X., et al., "Developing the production of environmentally friendly solvent oils for meeting the needs of the market economy," Shanghai Chemical Industry, vol. 31, No. 2, Feb. 2006, pp. 41-44.
Wang, Y. et al., "Gas chromatography analysis of crude oil and geological applications thereof," Geochemical, No. 4, Dec. 1979, pp. 292-307.
Zheng, W., et al., "Analysis of Termenoids in Petroleum Ether-Extracts of Eight Kinds of Plants of *Artemisia* Genus," Journal of Nanjing University, vol. 32, No. 4, Oct. 1996, pp. 706-711.

* cited by examiner

*Primary Examiner* — Jeffrey Washville

(74) *Attorney, Agent, or Firm* — Harness, Dickey & Pierce, P.L.C.

(57) ABSTRACT

Composition of special fluid comprising at least one hydrogenated mono- and/or at least one polyterpene, in a mixture with at least one special fluid for industrial applications such as the petroleum industry, in construction as sealants and paints, adhesives, the inks industry, metal working, the treatment and protection of metals, but also for domestic uses and in the agric-food and plumbing industries.

19 Claims, No Drawings

COMPOSITION OF SPECIAL FLUID AND USE

CROSS-REFERENCE TO RELATED APPLICATIONS

This application claims the benefit and priority of France Application No. 11 53 005, filed Apr. 6, 2011; the entire disclosure of which is incorporated herein by reference.

TECHNICAL FIELD

The present disclosure relates to a composition of special fluid comprising hydrogenated mono- and/or polyterpenes alone or in a mixture with special fluids of petroleum and/or synthetic origin for petroleum applications, for construction, printing, agri-food, pharmaceuticals, the automobile industry, industrial lubricants, domestic fuels, uses of fluids permitted for contact with food and for cosmetics.

PRIOR ART

The term special fluids refers to liquids used as industrial fluids, agricultural and horticultural fluids (for vegetable gardening (or market gardening) for the production of vegetables, growing fruit trees, for the production of fruits; floriculture for the production of ornamental plants; nurseries for the production of ligneous species, trees and shrubs, ornamental or not; greenhouse cultivation for flower and nursery production under glass), and fluids for domestic use, generally obtained from fossil hydrocarbons converted by refining routes but also from numerous products originating from the polymerization or oligomerization of olefins with 3 to 4 carbon atoms, and also from synthetic hydrocarbons resulting from the conversion of natural gas or of the synthesis gas originating from biomass and/or carbon. The latter include drilling fluids, industrial lubricants, fluids for formulations intended for the automobile industry, phytosanitary products, base fluids for formulating inks, fuels for domestic applications, sealant extender oils, viscosity reducers for resin-based formulations, pharmaceutical compositions and compositions for contact with food, fluids intended for cosmetic formulations.

The chemical nature and the composition of the fluids known to a person skilled in the art vary considerably depending on the envisaged application.

Certain special fluids are products obtained from the refining of crude oil, the properties of which are adapted to the envisaged application. Thus, the distillation range (measured by ASTM D86 or ASTM D1160 depending on the choice of final distillation point below or above 365° C.), the pour point (measured by ASTM D97), the viscosity at 20 or 40° C. (measured by ASTM D445), the density at 15° C. (measured by ASTM D4052), the sulphur content (measured by ASTM D5453), the aromatics content (measured by UV in the case of low contents or by HPLC IP391 in the case of higher contents), the aniline point (measured by ASTM D611) and the flash point (measured by ASTM D93) are determined. These properties and the method for producing these special fluids from hydrocarbons, in particular distilled from hydrocarbon cuts of petroleum origin, constitute important characteristics to be considered in order to adapt them to different envisaged applications. More particularly, these special fluids are obtained by hydrogenation of distillation cuts varying from 100 to 400° C., obtained by hydrocracking, by hydrotreatment, by catalytic cracking, by coking, by visbreaking and/or by hydrodewaxing. These special fluids are constituted predominantly by isoparaffins and saturated naphthenes, and have a sulphur content of less than 10 ppm as well as an aromatics content of less than 100 ppm.

For these various applications, narrow boiling point ranges between the initial distillation point (IBP) and the final distillation point (FBP) are often chosen, the narrowness of the cut making it possible to control the selectivity of the physicochemical characteristics, and in particular:

an adjusted flash point, an important parameter for satisfying safety requirements.

a narrower viscosity range for easier utilization, evaporation characteristics perfectly suited to applications requiring a drying stage of controlled duration, a defined surface tension value for certain applications requiring contact with materials and supports (metals, textiles, wood etc.), a high solvency defined by the aniline point value.

Obtaining narrow cuts is not always obvious, especially in the case of the reproduction of cuts of identical quality, sold for the same application as this requires access to resources of relatively constant compositions and to precise hydrogenation unit settings.

Other special fluids of synthetic origin result from the polymerization and/or oligomerization of olefins with 2 to 4 carbon atoms, this polymerization leading to products comprising from 2 to 5 olefin units per chain. They essentially contain normal paraffins and iso-paraffins, these fluids having distillation cuts and characteristics similar to those of fluids of petroleum origin. They are devoid of aromatic hydrocarbons and contain no sulphur-containing compounds.

Other special fluids can be obtained from the conversion of natural gas and/or carbon by conversion to synthesis gas, then according to the Fischer-Tropsch process to hydrocarbon compounds capable of being separated into distillation cuts with characteristics comparable to the special fluids described previously, i.e. without sulphur and essentially comprising paraffins and isoparaffins.

In the construction industry, numerous special fluids are used in construction materials, for example for floor coverings, paints, wallpapers and sealants for windows or plumbing joints, and all types of adhesives. They are in general constituted by one or two active components the viscosity of which is adjusted for the intended application by adding a hydrocarbon diluent of fossil, i.e. mainly petroleum, origin forming part of the special fluids. These diluents are mixed with at least one resin, a polymer and/or any other highviscosity paste and have a tendency, either immediately or over time, to evaporate and/or to degrade and to be a source of emissions which are often toxic to the environment and more particularly to human and animal health. These emissions are called VOC (volatile organic compounds) emissions. These emissions constitute a significant source of pollution inside homes, offices and premises and generally any closed space with limited ventilation, or in any case not directly open to air circulation.

Special fluids are also much used in particular in drilling fluids. In this application, fluids are particularly sought which are resistant to very high, or even extreme temperature and pressure conditions, in particular those encountered when drilling deep off-shore wells more than 4000 meters below sea level or in the polar regions or close to the latter. In fact, in deep seabed operations down to 5500 m, the temperature gradient between the entrance of the well and the bottom of the well can reach 200° C., the temperature at the entrance of the well being able to approach polar temperatures and the temperature at the bottom of well more than 160° C. The drilling fluids form part of the composition of the drilling muds at a rate of 30 to 95% by weight. These drilling muds play an essential role during on-shore or off-shore drilling operations, as they make it possible to lubricate the drilling tool (or bit) in order to limit its wear, but also to raise to the surface for treatment, excavated rock (cuttings) generated during the drilling and to maintain it in suspension during the phases when the circulation of the mud is stopped, and finally to maintain the pressure in the rock formation in order to prevent leaks and/or the collapse of walls. For this application, controlling the kinematic viscosity, the flash point, and the pour point is indispensable.

In ink applications, three main types of printing are conventionally used, which will require the use of different types of inks: relief printing, offset printing (or lithography) and photogravure printing. In the field of offset inks, depending on the type of drying it is possible to distinguish: so-called heatset inks for web-fed rotary printing, which dry by application of heat, inks for so-called sheetfed machines drying by absorption and oxidation, and also coldset inks (newspaper inks) which dry by absorption into the porous substrate.

For each of these applications, the composition of the inks is essential for obtaining the result. Printing inks are composed of pigments, binders, solvents and additives, but their distribution makes it possible to achieve the desired properties of the inks for each of the envisaged printing processes. The various requirements that must be met by the physical properties of high-volume printing products in particular, whilst taking economic criteria into account, impose severe constraints on the solvents used. On the one hand, the solvent must be capable of dissolving the binders as well as the various additives (controlled solvency), and on the other hand it must make it possible to achieve the viscosity and the tack in the desired range. In these applications, the products used must have optimum evaporation characteristics and lowest possible VOC emission level.

When used as lubricants, these fluids can be particularly effective for metal working, as fluids providing protection against oxidation or also electro-erosion or during rolling of aluminium. Their function is to minimize pressures and dissipate heat in metal working. They make it possible to reduce friction due to their lubricating properties, to clean parts, to limit their wear and protect them against corrosion, and to extend the life of the tools.

More generally the special fluids, by virtue of their characteristics, are liquid, odourless, and very pure as they have a reduced sulphur content, and are also devoid of toxic substances, in particular of mono- and polycyclic aromatic compounds. They are particularly suitable for applications requiring a short drying time and an adapted surface tension, having a small cut range. The level of purity also makes it possible to use them in the pharmaceuticals industry, for example in pharmaceutical excipients.

The present disclosure aims to remedy the problem of availability of special fluids of natural origin having characteristics close to those of special fluids currently used and available on the market. It also relates to the use of these novel special fluids to improve certain of the properties of standard special fluids, in particular low-temperature properties and lubricity in the case of low-temperature applications or even under extremely cold conditions.

SUMMARY

The purpose of the present disclosure is to use compounds of natural and renewable origin, which are non-toxic and virtually pure, having physico-chemical characteristics similar to those of special fluids, the stability and viscosity, but also the volatility level of which makes it possible to use them in the same applications as those intended for special fluids, optionally in more difficult environments or conditions of use.

A subject of the present disclosure is therefore a composition of special fluid comprising at least one hydrogenated mono- and/or at least one poly-terpene in a mixture with at least one special fluid of petroleum or synthetic origin. The invention relates more particularly to a composition comprising hydrogenated mono- and/or polyterpenes, i.e. completely saturated compounds with 2 to 5 isoprene units in linear and/or cyclic form chosen from the hydrogenated mono-, sesqui-, di- and sesterpenes. The mono- and/or poly-terpenes are chosen in particular from p-menthane, cis-pinane, limonane, trans-pinane, farnesane, cyclofarnesane, bisabolane, phytane, labdane and pristane. The completely saturated hydrogenated mono- and/or poly terpenes are preferably composed of 3 to 5 isoproprene units in linear and/or cyclic form chosen from the hydrogenated sesqui-, di- and sesterpenes of the group comprising farnesane, cyclofarnesane, bisabolane, phytane, labdane and pristane.

More particularly, the composition comprises at least one hydrogenated mono- or poly-terpene, alone or in combination with at least one other hydrogenated mono- or poly-terpene, in at least one special fluid compatible in terms of boiling temperature, flash point and density. The term "compatible" means that said at least one hydrogenated mono or polyterpene has a boiling temperature, a flash point and a density which are close to those of the special fluid(s).

More particularly, the composition comprises at least one hydrogenated mono- and/or poly terpene with a special fluid with a cut temperature comprised between 100 and 400° C., the distillation range of which is less than 75° C.

The special fluid is a hydrocarbonated mixture of potroleum or synthetic origin with a cut temperature comprised between 100 and 400° C., the distillation range of which is less than 75° C.

The special fluid according to the disclosure is obtained by hydrogenation of distillation cuts varying from 100 to 400° C., themselves obtained by hydrocracking, hydrotreatment, catalytic cracking, coking, vis-breaking and/or hydrodewaxing, and distillation of said cut, to cuts with a distillation range of less than 75° C. These special fluids are predominantly, i.e. more than 50% by weight, constituted by isoparaffins and naphthenes, have a sulphur content of less than 10 ppm and an aromatics content of less than 100 ppm. Preferably, the naphthenes content of these fluids is greater than 40% by weight, with more than 20% by weight being composed of polynaphthenes.

The special fluid can also originate from the polymerization and/or oligomerization of olefins with 2 to 4 carbon atoms, this polymerization leading to products comprising from 2 to 5 olefin units per chain. They essentially contain normal paraffins and iso-paraffins.

Another special fluid can be obtained from the conversion of natural gas and/or carbon by conversion to synthesis gas, then according to the Fischer-Tropsch process, to hydrocarbon compounds capable of being separated, after hydrogenation, into distillation cuts with cuts comprised between 100 and 400° C. and with a distillation range of less than 75° C., the sulphur content being less than or equal to 10 ppm and the aromatic content being less than 100 ppm.

According to a first embodiment, the composition comprises at least one hydrogenated mono-terpene chosen from p-menthane, cis-pinane, trans-pinane alone or in combination with at least one special fluid with a cut temperature comprised between 160 and 250° C., with a density comprised between 750 and 870 kg/m³, a flash point below 100° C., but above 30° C.

According to a second embodiment, the composition comprises at least one hydrogenated sesqui-terpene such as farnesane, cyclofarnesane, bisabolane, alone or in combination with at least one special fluid with a cut temperature comprised between 230 and 290° C., a density comprised between 760 and 820 kg/m³, and a flash point above 100° C.

According to a third embodiment, the composition comprises at least one diterpene chosen from phytane, labdane and pristane, alone or in combination with at least one special fluid with a cut temperature comprised between 300 and 350° C., with a density comprised between 780 and 830 kg/m³, and a flash point above 130° C.

According to a fourth embodiment, the composition comprises at least one hydrogenated di-terpene from the group comprising phytane, labdane and pristane, alone or in combination with at least one special fluid with a cut temperature above 300° C., preferably comprised between 350 and 425° C., with a density comprised between 790 and 840 kg/m³, a flash point above 130° C. and viscosity varying from 6.5 to 11 mm²/s.

A second subject of the disclosure is the use of the composition of special fluid for industrial applications such as in the petroleum industry, in construction as sealants and paints, adhesives, the inks industry, metal working, the treatment and protection of metals, but also for domestic uses, in the agri-food, automobile, plumbing and pharmaceutical industries, for industrial lubricants, domestic fuels, and applications of fluids permitted for contact with food and for cosmetics.

More particularly, the use according to the present disclosure corresponds to different applications, in particular:

in resins, paints, varnishes, adhesives and cleaning agents for degreasing with regard to compositions comprising hydrogenated mono-terpenes, in inks, as drilling fluid, for working aluminium or as cleaning/degreasing agent in the case of compositions containing hydrogenated sesqui-terpenes, in particular farnesane, in printing inks, as lubricants, as drilling fluid, in the pharmaceuticals and cosmetics industries, in sealants, or in phytosanitary products, and for the treatment of textiles and metals in the case of compositions containing hydrogenated di-terpenes, and finally as lubricants, for the production of pharmaceutical excipients and for the treatment of textiles and metals, and also for applications in sealants in the case of compositions containing at least one hydrogenated di-terpene, alone or in a mixture with at least one special fluid with cut temperatures above 350° C.

DETAILED DESCRIPTION

The hydrogenated terpenes introduced into the composition according to the disclosure are obtained by hydrogenation of the terpenes originating from numerous plants, in particular conifers. These are major components of natural resins and essences produced from these resins such as turpentine oil. They can also be produced by any other biosynthesis process from sugars or biomass. These hydrogenated terpenes constitute a novel base source for special fluids provided that they are liquid at ambient temperature, and that they are obtained from renewable natural substances, that they contain no sulphur and less than 100 ppm of aromatic compounds. They are particularly advantageous in that they can be produced with a high degree of purity, for example more than 95% purity necessary for certain envisaged applications. They have very precise characteristics in terms of boiling temperature, very low pour point, rapid drying ability (in the case of certain of them), absence of sulphur and toxic components, with a viscosity suited to the intended applications and finally they are typically non-VOC-emitters (in compliance with the AgBB-type emissions reduction scheme (Germany), satisfying quality or ecolabel standards such as GEV Emicode, Blue Angel, US Greenguard etc.) and therefore only slightly toxic to the environment and when handled by workers. Without aromatic compounds, they are only slightly toxic.

In order to implement the disclosure, these hydrogenated terpenes will advantageously comprise from 2 to 5 isoprene units in linear and/or cyclic form. In fact, the hydrogenation of isoprene compounds can lead to the formation of linear, branched and cyclic compounds, these compounds being able to be obtained alone or in a mixture in the final hydrogenated product.

It will preferably be chosen to hydrogenate mono- and poly-terpenes such as the mono-, sesqui-, di- and ses-terpenes, the preferred hydrogenated products corresponding to the following compounds: p-menthane, cis-pinane, trans-pinane, limonane, farnesane, cyclofarnesane, bisabolane, phytane, labdane and pristine.

In order to hydrogenate these terpenes, it is possible to use any type of hydrogenation known to a person skilled in the art, for example under a pressure of 30 to 80 bars, at a temperature comprised between 130 and 250° C. in the presence of a hydrogenation catalyst composed of at least one metal of Group VIII such as nickel, cobalt, molybdenum, tungsten, platinum and/or palladium supported by at least one metallic oxide from the group constituted by silica, alumina, zirconium and/or titanium oxide, crystalline or amorphous, or also a zeolite.

These hydrogenated terpenes can be used alone or in a mixture and also optionally in a mixture with conventional special fluids such as those originating from (sane, Ketrul, Spirdane, Hydroseal, Scriptane, Eolane and Gemseal ranges from TOTAL FLUIDS or also ranges such as ISOPAR from Exxon, Shellsol from Shell, Nexbase from Neste Oil, IP clean and IP solvent from Idemitsu Kosan or also SK-Isol G from SK solvent essentially comprising isoparaffins and/or naphthenes.

The addition of these hydrogenated terpenes to conventional special fluids can in particular allow adjustment of the low-temperature properties, in particular reduction of the pour point of said fluid, adjustment of its solvency and therefore its aniline point, or also limitation of VOC emissions linked to the dilution of certain compounds emitting more VOC. It is also possible to adjust the density, and/or the viscosity of a composition. Thus, special fluids currently proposed for other applications can be used in new applications due to the introduction of appropriate hydrogenated terpenes in a mixture therewith.

More particularly, the composition can comprise at least one hydrogenated mono- and/or poly-terpene, alone or in combination with at least one other hydrogenated mono- or poly-terpene, and optionally at least one special fluid compatible in terms of boiling temperature, flash point and density.

Thus, these hydrogenated terpenes, alone or in a mixture, make it possible to adjust the characteristics of at least one special fluid with a cut temperature comprised between 100 and 400° C., for which the temperature range of said cut is less than 75° C.

Thus, according to a method for implementing the disclosure, a composition which can be used in resins, paints, varnishes, adhesives, sealants, in particular silicone, modified silane, polyurethane and/or acrylic sealants, or for degreasing/cleaning walls, comprises at least one hydrogenated terpene from the group constituted by the hydrogenated mono- and sesqui-terpenes such as p-menthane, cis-pinane, trans-pinane, limonane, farnesane, cyclofarnesane, or also bisabolane. For these applications, these hydrogenated terpenes can be mixed with at least one special fluid with a cut temperature comprised between 180 and 290° C., with a density comprised between 750 and 820 kg/m$^3$, and viscosity at 40° C. determined by the standard ASTM D445 of less than 4 mm$^2$/s. Among the special fluids conventionally used for these applications, these hydrogenated terpenes are easily mixed with SPIRDANE D40, D60, ISANE IP140, IP175, IP185, or IP200 or also EDC 99DW and EDC 95-11 sold by Total Fluids. Among other special fluids which can be used in a mixture, ISOPAR from EXXONMOBIL CHEMICAL, SOFTROL 100 from CHEVRON PHILLIPS Chemical or also the Shellsol range from Shell can more particularly be mentioned.

For printing ink applications, depending on the desired viscosity, the compositions according to the disclosure include hydrogenated sesqui-, di- or ses-terpenes alone or in a mixture with at least one special fluid suited to said application. Thus, a composition according to the disclosure can comprise farnesane in a mixture with special fluids with boiling temperatures comprised between 230 and 360° C., with a density comprised between 760 and 820 kg/m$^3$, and a flash point above 100° C., and the viscosity of which measured at 40° C. is comprised between 2 and 6.5 mm$^2$/s. Thus, these hydrogenated terpenes can be used alone or in a mixture with commercial products such as those of the Scriptane range from Total Fluids, but also other commercial products on the market.

Another composition suitable for applications such as lubricants for metal working, sealants and adhesives, polymer dilution solvents, in the phytosanitary, pharmaceuticals and cosmetics industries, in printing inks composed of phytane, labdane and/or pristane alone or in a mixture with a special fluid with a cut temperature comprised between 230 and 360° C., with a density comprised between 790 and 830 kg/m$^3$, and a flash point above 130° C. and a viscosity at 40° C. comprised between 3 and 11 mm$^2$/s. Said composition according to the disclosure can also comprise in a mixture with the at least one of the phytane, labdane and/or pristane compounds, cuts of the HYDROSEAL G232H, HYDROSEAL G240H, HYDROSEAL G250H, HYDROSEAL G270H, HYDROSEAL G3H, HYDROSEAL G400H, HYDROSEAL G290H, HYDROSEAL G340H, SCRIPTANE PW24/27H, Scriptane PW25/28H, Scriptane PW26/29H, Scriptane PW28/32H and Scriptane PW30/35H type sold by Total Fluids. The other special fluids which can be used include EXXSOL D110, D120, D130 and D140 sold by EXXONMOBIL CHEMICAL, CONOSOL C200 and C260 from CONOCO PHILLIPS, and Calumet LVP200 from Calumet, Poliot 261 and LVP200 from Petrochem Carless or also YK2831 and YKD 130 from SK.

A third composition, with a boiling temperature above 350° C. advantageously comprises at least one hydrogenated sesqui- and/or ses-terpene alone or in a mixture with a special fluid with a cut temperature above 280° C., a flash point above 140° C., and a viscosity measured at 40° C. greater than 7 mm$^2$/s. This composition can be used for producing pharmaceutical excipients. By mixing a hydrogenated di-terpene with HYDROSEAL G340H, compositions with low VOC emissions are obtained (in compliance with the AgBB-type emissions reduction scheme (Germany), with quality or eco-label standards such as GEV Emicode, Blue Angel, US Greenguard etc.); these compositions can also be used in other applications such as construction materials, and materials for the automobile industry. These compositions can be also used advantageously in mixtures of elastomers, in lubricants or fluids for metal working, in particular working aluminium. They can also be used for phytosanitary applications.

For drilling applications, farnesane is preferred among the hydrogenated terpenes used according to the disclosure. It can be used alone or in a mixture with special fluids with a cut temperature comprised between 230 and 290° C., with a density comprised between 760 and 820 kg/m$^3$, and a flash point above 100° C. Among the latter, EDC 99DW, EDC 95-11, EDC Diamond or EDC PEARL sold by Total Fluids are preferably mixed with farnesane, the viscosities being able to be adjusted between 2 and 5 mm$^2$/s in certain applications.

For phytosanitary applications, the hydrogenated diterpenes comprising phytane, labdane, pristane, can be used alone or in combination, in a mixture with at least one special fluid with a cut temperature comprised between 300 and 400° C., with a density comprised between 800 and 830 kg/m$^3$, and a flash point above 130 and a viscosity at 40° C. greater than 4, preferably greater than 7, but less than 15 mm$^2$/s. Among the phytosanitary fluids available on the market, these hydrogenated terpenes can be used in a mixture with GENERA, BANOLE, CITROLE, OVISPRAY, CATANE and FINAVESTAN, sold for the protection of fruits and vegetable by spreading on the crops during their growth, these products being sold by Total Fluids.

Special fluids mixed with one of the hydrogenated terpenes will preferably have the smallest possible distillation cut range, preferably less than 75° C. and preferably less than 50° C. in order to obtain all the qualities required for the intended applications.

For metal working and/or textile applications, mixtures with HYDROSEAL G232H, G250H, G3H, G290H, G340H and G400H are preferred, or also LUBRILAM S40L or also LUBRILAM S50L for rolling aluminium.

The examples hereafter are intended to illustrate exemplary embodiments of the invention and cannot be used to limit its scope.

EXAMPLE 1

The present example aims to compare the properties of farnesane obtained by hydrogenation of farnesene, hydrogenated sesqui-terpene with those of the special fluids commonly used for various applications and the possible mixtures of farnesane with other special fluids.

Table I below shows the physico-chemical characteristics of farnesane and of the commercial special fluids as well as a 50/50 mixture of farnesane/special fluid for a drilling application.

TABLE I

| | Units | Method | Farnesane | EDC99DW | Ketrul D80 | Ketrul/Farnesane 50/50 by weight |
|---|---|---|---|---|---|---|
| Properties | | | | | | |
| Appearance | — | | Clear | clear | clear | clear |
| Density at 15° C. | kg/m3 | NF EN ISO 12185 | 774 | 811 | 811 | 791.97 |
| Viscosity at 40° C. | mm²/s | EN ISO 3104 | 2.5 | 2.30 | 1.70 | 1.96 |
| Pour point | ° C. | T 60 105 | <−71 | −51 | −51 | −67 |
| Flash point | ° C. | EN ISO 2719 | 103.0 | 101 | 76 | 85 |
| Aromatics content | ppm | UV | 0 | 25 | <20 | <20 |
| Total sulphur | ppm | FX/D2622 | — | <1 | <1 | <1 |
| Distillation | | | | | | |
| Initial point | ° C. | EN ISO 3405 | 242 | 230 | 201 | 201 |
| End point | ° C. | EN ISO 3405 | 271 | 270 | 239 | 270 |

For drilling application, it is well known to use EDC99DW which has the best characteristics.

It is noted that the properties of farnesane, in particular its viscosity, its pour point, its boiling temperature and its flash point make this product a good drilling fluid. By contrast, Ketrul D80, which cannot be used in this application because its flash point is too low, can be used in a 50/50 by weight mixture with farnesane: the flash point rises above 80° C. which makes it possible to achieve a good level of safety with this mixture and a means of remedying the deficiencies of EDC99DW in particular. Farnesane also improves the pour point which makes this mixture particularly effective in cold regions.

The Scriptane range from Total fluids is particularly suitable as a solvent in inks: Table II below compares the properties of Scriptane 25/28 used for certain ink applications with those of a Scriptane 24/27H unsuitable for this application, and with those of farnesane.

TABLE II

| | Units | Method | Farnesane | Scriptane 25/28H | Scriptane 24/27H | Scriptane 24/27H/Farnesane 50/50 by weight |
|---|---|---|---|---|---|---|
| Properties | | | | | | |
| Appearance | — | | Clear | clear | clear | clear |
| Density at 15° C. | kg/m3 | NF EN ISO 12185 | 774 | 815 | 817 | 793.97 |
| Viscosity at 40° C. | mm²/s | EN ISO 3104 | 2.5 | 2.8 | 2.4 | 2.3 |
| Pour point | ° C. | T 60 105 | <−71 | −40 | −50 | −66 |
| Flash point | ° C. | EN ISO 2719 | 103.0 | 114 | 103 | 103 |
| Aniline point | ° C. | EN ISO 2977 | >87 | 87 | 79 | 84 |
| Aromatics content | ppm | UV | 0 | 50 | 50 | 50 |
| Total sulphur | ppm | FX/D2622 | — | <1 | <1 | <1 |
| Distillation | | | | | | |
| Initial point | ° C. | EN ISO 3405 | 242 | 251 | 237 | 237 |
| End point | ° C. | EN ISO 3405 | 271 | 281 | 262 | 271 |

It is noted that farnesane makes it possible to achieve characteristics of the Scriptane 25/28H with a narrower cut: the viscosity is comparable, and the pour point better.

For metal working, in particular the rolling of aluminium, it is customary to use lubricants with the name Lubrilam. Table III shows the physico-chemical characteristics of two Lubrilam fluids and farnesane alone and in a 50/50 by weight mixture with Lubrilam S50L.

TABLE III

|  | Units | Method | Farnesane | LUBRILAM S40L | LUBRILAM S50L | LUBRILAM S50L/Farnesane 50/50 by weight |
|---|---|---|---|---|---|---|
| Properties |  |  |  |  |  |  |
| Appearance | — |  | Clear | clear | clear | clear |
| Density at 15° C. | kg/m3 | NF EN ISO 12185 | 774 | 820 | 817 | 794.97 |
| Viscosity at 40° C. | mm²/s | EN ISO 3104 | 2.5 | 2.4 | 2.8 | 2.4 |
| Pour point | ° C. | T 60 105 | <−71 | −50 | −40 | <−70 |
| Flash point | ° C. | EN ISO 2719 | 103.0 | 103 | 116 | 111 |
| Aromatics content | ppm | UV | 0 | 30 | 30 | <30 |
| Total sulphur | ppm | FX/D26 22 | <2 | <2 | <2 | <2 |
| Distillation |  |  |  |  |  |  |
| Initial point | ° C. | EN ISO 3405 | 242 | 236 | 254 | 245 |
| End point | ° C. | EN ISO 3405 | 271 | 262 | 282 | 270 |

It is noted that farnesane alone can be substituted for Lubrilam S40L. The 50/50 by weight mixture of farnesane with Lubrilam S50L can also be suitable.

EXAMPLE 2

The present example relates to the application in paints of the compositions of the disclosures comprising pinane and having a high solvency without the drawbacks of standard aromatic solvents.

Ideally, a highly aromatic solvent with a low aniline point and a narrow distillation cut is preferred in order to ensure a good solvency and a controlled drying time. Solvarex 9 from Total Fluids, corresponding to a C9 aromatic cut (comprising 9 carbon atoms) having an aniline point of 14 and a distillation cut varying from 160 to 175° C. is therefore particularly valued. However, due to the regulatory restrictions on the use of highly aromatic products, it has been replaced by dearomatized white spirits in the compositions of decorative and industrial paints, these white spirits having a flash point of 40° C., such as for example Spirdane D40 the aniline point of which is 68 and the distillation cut is comprised between 156 and 198° C.

Table IV below gives the characteristics of the compositions of special fluids containing aromatic compounds, dearomatized compounds and 50/50 mixtures of Pinane and dearomatized compounds.

TABLE IV

|  | Units | Method | Pinane | Spirdane D40/Pinane 50/50 | Solvarex 9/C9 aromatic fluid | Spirdane D40/ dearomatized white spirit |
|---|---|---|---|---|---|---|
| Properties |  |  |  |  |  |  |
| Appearance | — |  | Light & clear | Light & clear | Light & clear | Light & clear |
| Density at 15° C. | kg/m³ | NF EN ISO 12185 | 861.4 | 818.2 | 875 | 775 |
| Saybolt colour |  | NF M 07003 | >+30 | >+30 | >+30 | >+30 |
| Viscosity at 20° C. | mm²/s | EN ISO 3104 | 2.655 | 1.7 | 0.95 | 1.1 |
| Viscosity at 40° C. | mm²/s | EN ISO 3104 | 2.5 | 2.4 | 2.8 | 2.4 |
| Aniline point |  | ASTM D611 | 40.7 | 55 | 14 | 68 |

TABLE IV-continued

| Properties | Units | Method | Pinane | Spirdane D40/Pinane 50/50 | Solvarex 9/C9 aromatic fluid | Spirdane D40/ dearomatized white spirit |
|---|---|---|---|---|---|---|
| Pour point | °C. | T 60 105 | <−72 | <−50 | <−50 | <−50 |
| Flash point | °C. | EN ISO 2719 | 45 | 44 | 43 | 44 |
| Aromatics content | ppm | UV | 0 | 0 | 99.5 | 0 |
| Distillation | | | | | | |
| Initial point | °C. | EN ISO 3405 | 164.5 | 160 | 160 | 156 |
| End point | °C. | EN ISO 3405 | 165.5 | 188 | 175 | 198 |

It is noted that pinane used in a mixture with dearomatized white spirit improves the solvency of these white spirits (lowering of the aniline point from 68 to 55) and reduces the width of the cut of the latter. Moreover, the pinane makes it possible to improve the volatility and the drying time of the formulations is reduced. Of course, it is possible to adjust the pinane:dearomatized white spirit ratio in order to optimize the drying time.

EXAMPLE 3

The present example relates to the use of pinane in compositions according to the disclosure used for cleaning industrial tools and metal parts. The concern here is to improve control of the volatility of the products used for the cleaning.

Generally, ISANE 155 type isoparaffins sold by Total Fluids are used, or also a ISOPAR sold by EXXON Chemical which have narrow distillation cut ranges and therefore a narrow drying temperature range, ideal for the flash drying process (*). However, these isoparaffins, ISANES or ISOPAR have a low solvency. Table V below gives the characteristics of ISANE IP155, those of pinane and those of a 50/50 mixture of pinane and ISANE IP155.

(*) The flash process makes it possible to remove the solvent by bringing the cleaned surface to a suitable temperature for a very short time in order to vaporize the solvent.

TABLE V

| Properties | Units | Method | Pinane | ISANE IP155 | ISANE IP155/ pinane 50/50 |
|---|---|---|---|---|---|
| Appearance | | | Light & clear | Light & clear | Light & clear |
| Density at 15° C. | kg/m³ | NF EN ISO 12185 | 861.4 | 746 | 799 |
| Saybolt colour | | NF M 07003 | >+30 | >+30 | >+30 |
| Viscosity at 20° C. | mm²/s | EN ISO 3104 | 2.655 | 1.2 | 2.1 |
| Viscosity at 40° C. | mm²/s | EN ISO 3104 | 2.5 | 1 | 1.8 |
| Aniline point | | ASTM D611 | 40.7 | 78 | 61 |
| Pour point | °C. | T 60 105 | <−72 | <−50 | −62 |
| Aromatics content | ppm | UV | 0 | 0 | 0 |
| Distillation | | | | | |
| Initial point | °C. | EN ISO 3405 | 164.5 | 158 | 160 |
| End point | °C. | EN ISO 3405 | 165.5 | 175 | 169 |

It is noted from this table that the use of pinane in a mixture with isoparaffins normally used for cleaning parts and/or industrial tools makes it possible to clearly improve its solvency which is linked to the value of the aniline point.

EXAMPLE 4

The present example relates to the use of phytane in compositions of the disclosure in particular for all the industrial applications (silicone sealants and lubricants in particular) requiring good fluidity at a low temperature under severe conditions of use or storage. The phytane can be used as it is or in a mixture with Hydroseal 310 H which is a dearomatized and isodewaxed hydrocarbon fluid.

TABLE VI

| Properties | Units | Method | Phytane | Hydroseal G310H | Phytane Hydroseal G310 H 50/50 |
|---|---|---|---|---|---|
| Appearance | | | Light & clear | Light & clear | Light & clear |
| Density at 15° C. | kg/m3 | NF EN ISO 12185 | 791 | 818 | 809 |
| Saybolt colour | | NF M 07003 | | <0.5 | <0.5 |
| Viscosity at 20° C. | mm²/s | EN ISO 3104 | 12 | 10.9 | 11.4 |
| Viscosity at 40° C. | mm²/s | EN ISO 3104 | 5.9 | 6.0 | 5.9 |
| Aniline point | | ASTM D611 | 92 | 99 | 98 |
| Pour point | °C. | T 60 105 | <−30 | <−18 | −27 |
| Aromatics content | ppm | UV | 0 | 0 | 0 |
| Distillation | | | | | |
| Initial point | °C. | ASTM D86 | 322 | 300 | 300 |
| End point | °C. | ASTM D86 | 324 | 350 | 350 |

The phytane-based fluids are particularly efficient at low temperatures, having a pour point below −24° C. which is particularly desirable when operating at low temperatures or when the finished products are kept at such temperatures over a long period.

What is claimed is:

1. Composition of special fluid comprising at least one hydrogenated polyterpene selected from the group consisting of hydrogenated sesquiterpenes, and hydrogenated sesterpenes, in a mixture with at least one special fluid, said special fluid being a hydrocarbonated mixture of petroleum or synthetic origin with cut temperatures comprised between 180 and 360° C., the distillation range of which is less than 75° C.

2. Composition according to claim 1, in which the polyterpenes are selected from the group consisting of farnesane, cyclofarnesane, bisabolane.

3. Composition according to claim 1, characterized in that the special fluid is obtained by hydrogenation of distillation cuts varying from 180 to 400° C., themselves obtained by hydrocracking, by hydrotreatment, by catalytic cracking, by coking, by vis-breaking and/or by hydrodewaxing, and distillation of said cuts into cuts with a distillation range of less than 75° C., and comprising less than 10 ppm of sulphur and less than 100 ppm of aromatic compounds.

4. Composition according to claim 1, characterized in that the special fluid originates from the polymerization and/or oligomerization of olefins with 2 to 4 carbon atoms, this polymerization leading to products comprising from 2 to 5 olefin units per chain, and containing paraffins and isoparaffins.

5. Composition according to claim 1, characterized in that the special fluid is obtained from the conversion of natural gas and/or carbon by conversion to synthesis gas then according to the Fischer-Tropsch process to hydrocarbon compounds capable of being separated after hydrogenation into distillation cuts with cuts comprised between 180 and 400° C. and with a distillation range of less than 75° C., the sulphur content being less than or equal to 10 ppm and the aromatics content less than 100 ppm.

6. Composition according to claim 1, comprising at least one hydrogenated sesquiterpene selected from the group consisting of farnesane, cyclofarnesane and bisabolane in combination with at least one special fluid with a cut temperature comprised between 230 and 290° C., with a density comprised between 760 and 820 kg/m$^3$, and a flash point above 100° C.

7. Composition according to claim 1, used in the petroleum industry, construction, domestic uses, the automobile, agric-food, pharmaceutical industries, for industrial lubricants, domestic fuels, and applications of fluids permitted for contact with food.

8. Composition according to claim 7, used in inks, as drilling fluid, for working aluminium or as a cleaning/degreasing agent, said composition comprising hydrogenated sesqui-terpenes.

9. Composition according to claim 7, used in printing inks, as lubricants, as drilling fluid, in the pharmaceuticals industry, in sealants, in phytosanitary products and for the treatment of textiles and metals, said composition comprising hydrogenated di-terpenes.

10. Composition according to claim 7, used as lubricants, for the production of pharmaceutical excipients, for the treatment of textiles and metals, and for applications for sealants, said composition comprising at least one hydrogenated di-terpene, in a mixture with at least one special fluid with a cut temperature above 350° C.

11. Composition according to claim 1, wherein said special fluid is a hydrocarbonated mixture of petroleum or synthetic origin with cut temperatures comprised between 230 and 360° C., the distillation range of which is less than 75° C.

12. Composition according to claim 1, characterized in that the special fluid is obtained by hydrogenation of distillation cuts varying from 230 to 360° C., themselves obtained by hydrocracking, by hydrotreatment, by catalytic cracking, by coking, by vis-breaking and/or by hydrodewaxing, and distillation of said cuts into cuts with a distillation range of less than 75° C., and comprising less than 10 ppm of sulphur and less than 100 ppm of aromatic compounds.

13. Composition of special fluid comprising at least one hydrogenated diterpene selected from the group consisting of phytane, labdane and pristane, and at least one component selected from the group consisting of hydrogenated monoterpenes, hydrogenated sesquiterpenes, and hydrogenated sesterpenes, the at least one hydrogenated diterpene and the at least one component being in a mixture with at least one special fluid, said special fluid being a hydrocarbonated mixture of petroleum or synthetic origin with a cut temperature greater than or equal to 300° C., with a density comprised between 790 and 840 kg/m$^3$, and a flash point above 130° C.

14. Composition according to claim 13, wherein the hydrocarbonated mixture of petroleum or synthetic origin has a cut temperature comprised between 300 and 350° C., and a density comprised between 800 and 830 kg/m$^3$.

15. Composition according to claim 13, wherein the hydrocarbonated mixture of petroleum or synthetic origin has a cut temperature comprised between 350 and 425° C.

16. Composition according to claim 13, wherein the hydrocarbonated mixture of petroleum or synthetic origin has density comprised between 800 and 830 kg/m$^3$.

17. Composition according to claim 13, wherein the hydrocarbonated mixture of petroleum or synthetic origin has a viscosity varying from 6.5 to 11 mm$^2$/s.

18. Composition according to claim 13, wherein the composition comprises at least one hydrogenated sesquiterpene selected from the group consisting of farnesane, cyclofarnesane and bisabolane.

19. Composition according to claim 8, wherein the hydrogenated sesquiterpene is farnesane.

* * * * *